(12) United States Patent
Dutta

(10) Patent No.: US 6,589,464 B1
(45) Date of Patent: Jul. 8, 2003

(54) LUBRICIOUS CATHETER SHAFT

(75) Inventor: Debashis Dutta, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 283 days.

(21) Appl. No.: 09/656,497

(22) Filed: Sep. 7, 2000

Related U.S. Application Data

(62) Division of application No. 09/173,478, filed on Oct. 14, 1998, now Pat. No. 6,165,158.

(51) Int. Cl.[7] ............................................. B29C 47/00
(52) U.S. Cl. ............................ 264/171.26; 264/209.3; 264/288.4
(58) Field of Search .......................... 264/171.1, 171.26, 264/171.28, 171.29, 209.3, 209.4, 209.5, 288.4, 108

(56) References Cited

U.S. PATENT DOCUMENTS

| | | | |
|---|---|---|---|
| 3,458,596 A | 7/1969 | Faigle | 260/857 |
| 4,234,535 A | 11/1980 | Okita | 264/519 |
| 4,362,163 A | 12/1982 | Krick | 604/280 |
| 4,642,267 A | 2/1987 | Creasy et al. | 428/413 |
| 4,789,720 A | 12/1988 | Teffenhart | 528/76 |
| 4,822,615 A | 4/1989 | Iwata et al. | 424/423 |
| 4,838,877 A | 6/1989 | Massau | 604/272 |
| 4,847,324 A | 7/1989 | Creasy | 525/71 |
| 4,875,287 A | 10/1989 | Creasy et al. | 30/34.01 |
| 4,883,699 A | 11/1989 | Aniuk et al. | 428/36.9 |
| 4,898,591 A | 2/1990 | Jang et al. | 604/282 |
| 4,920,172 A | 4/1990 | Daoud | 524/502 |
| 4,945,126 A | 7/1990 | Crosby et al. | 524/507 |
| 5,061,424 A | 10/1991 | Karimi et al. | 264/171 |
| 5,156,785 A * | 10/1992 | Zdrahala | 264/108 |
| 5,270,086 A | 12/1993 | Hamlin | 428/35.2 |
| 5,281,677 A | 1/1994 | Onwunaka et al. | 525/458 |
| 5,304,134 A | 4/1994 | Kraus et al. | 604/96 |
| 5,322,659 A | 6/1994 | Walder et al. | 264/171 |
| 5,334,169 A | 8/1994 | Brown et al. | 604/282 |
| 5,453,099 A | 9/1995 | Lee et al. | 604/282 |
| 5,563,233 A | 10/1996 | Reich et al. | 528/76 |
| 5,589,545 A | 12/1996 | Ramachandran et al. | 525/184 |
| 5,614,136 A * | 3/1997 | Pepin et al. | 264/40.3 |
| 5,641,373 A | 6/1997 | Shannon et al. | 156/242 |
| 5,645,931 A | 7/1997 | Fan et al. | 428/334 |
| 5,648,088 A | 7/1997 | Bezwada et al. | 424/426 |

(List continued on next page.)

FOREIGN PATENT DOCUMENTS

| | | |
|---|---|---|
| EP | 0124955 A | 11/1983 |
| WO | 97/26027 A | 7/1997 |

OTHER PUBLICATIONS

Encyclopedia of Polymer Science and Engineering, vol. 12, p. 417–419, 1989.*
Concise Encyclopedia of Polymer Science and Engineering, pp. 830–835, 1990.*

Primary Examiner—Mark Eashoo
(74) Attorney, Agent, or Firm—Fulwider Patton Lee & Utecht, LLP

(57) ABSTRACT

An intravascular catheter which has a lubricious catheter shaft formed from a polymeric blend comprising a thermoplastic polymeric component and a lubricious polymeric component. The lubricious polymeric component is immiscible in the thermoplastic polymeric component and exists as elongated fibers having a high aspect ratio. The lubricious component exists as a separate phase of elongated fibers which provide improved lubricity to an extruded catheter shaft formed of the polymeric blend of the invention. The aspect ratio of the lubricious component fibers is about 10 to about 100, and preferably at least about 20. The high aspect ratio of the lubricious component fibers increase the surface area of the lubricious component on the surface of the catheter shaft, and consequently increase the lubricity of the catheter shaft.

4 Claims, 2 Drawing Sheets

U.S. PATENT DOCUMENTS

| | | |
|---|---|---|
| 5,662,960 A | 9/1997 | Hostettler et al. ............ 427/2.3 |
| 5,820,594 A | 10/1998 | Fontirroche et al. ........... 604/96 |
| 5,849,368 A | 12/1998 | Hostettler et al. ........... 427/536 |
| 5,868,719 A | 2/1999 | Tsukernik ................... 604/265 |
| 5,921,957 A | 7/1999 | Killion et al. ................ 604/96 |
| 6,165,158 A * | 12/2000 | Dutta ......................... 604/265 |

* cited by examiner

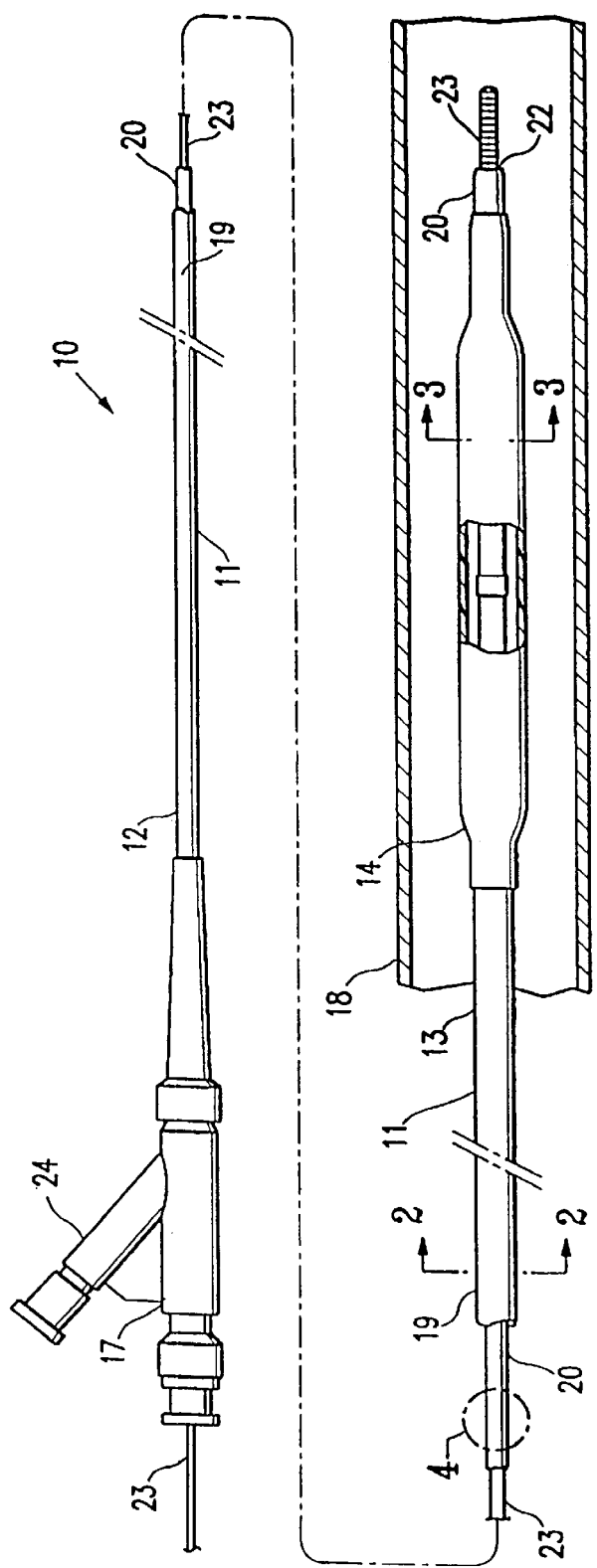
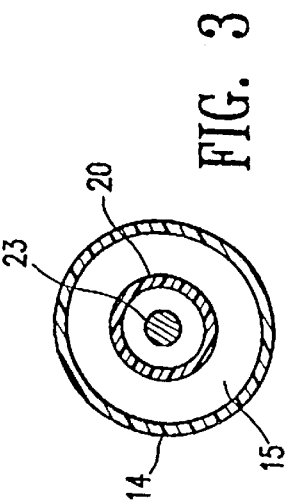
FIG. 1
FIG. 2
FIG. 3

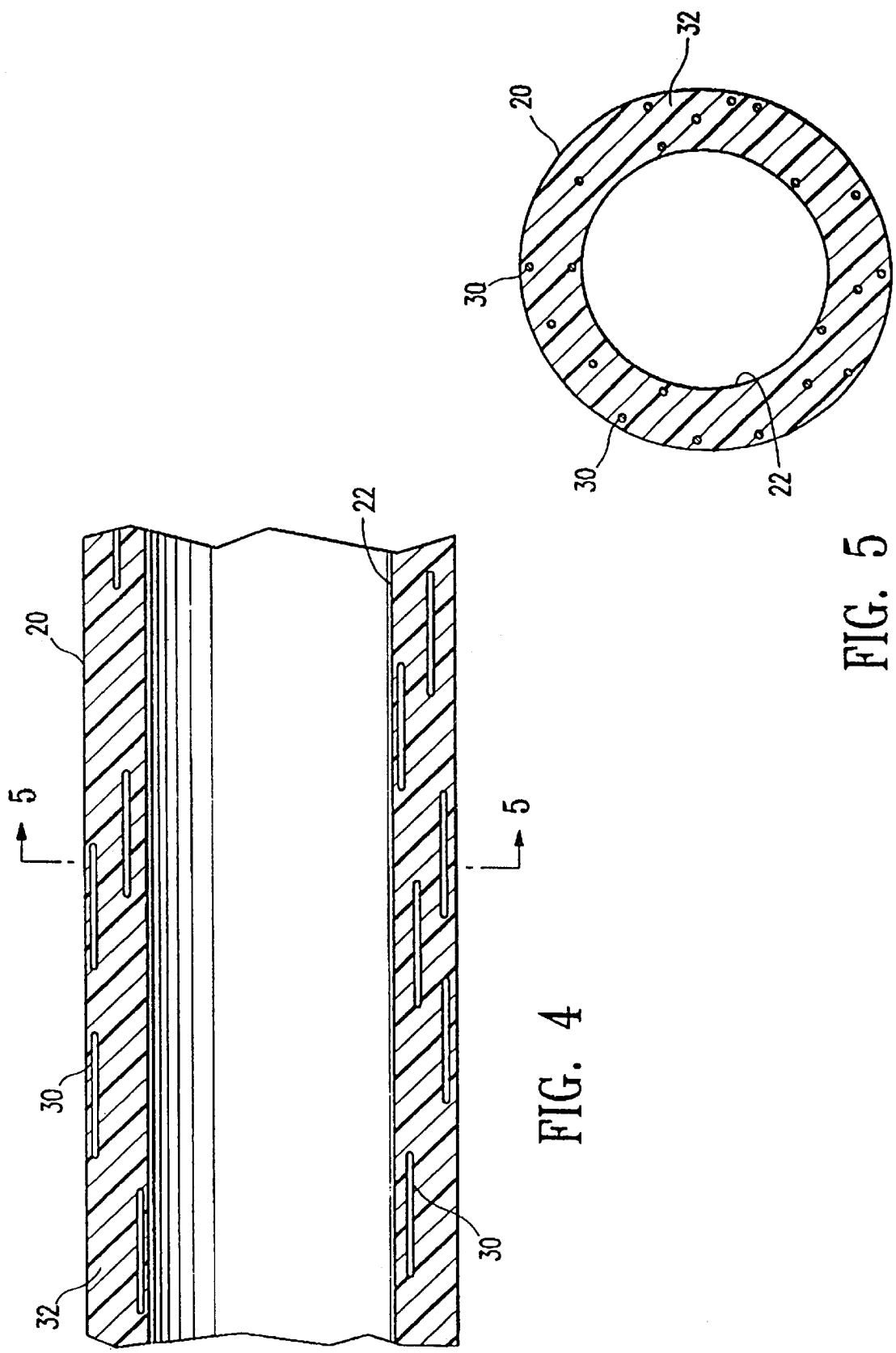

LUBRICIOUS CATHETER SHAFT

This application is a continuation of application Ser. No. 09/173,478, of Debadshis Dutta, for LUBRICIOUS CATHETER SHAFT, filed on Oct. 14, 1998; now U.S. Pat. No. 6,165,158, incorporated herein by reference in its entirety.

BACKGROUND OF THE INVENTION this invention relates to the field of intravascular catheters, and more particularly to a catheter with a lubricious catheter shaft and a method of manufacture thereof. In percutaneous transluminal coronary angioplasty (PTCA) a balloon catheter is used to restore free flow in a clogged coronary vessel. The catheter is maneuvered through the patient's tortuous anatomy and into the patients coronary anatomy until the balloon is properly positioned across the stenosis to be dilated. Once properly positioned, the balloon is inflated with liquid one or more times to a predetermined size at relatively high pressures (e.g. greater than 4 atm) to reopen the coronary passageway. After the balloon is finally deflated, blood flow resumes through the dilated artery and the balloon catheter can be removed therefrom.

Balloon catheters generally comprise an elongated shaft with an inflatable balloon on the distal end of the shaft. An inflation lumen extending within the shaft is used to deliver inflation fluid to the balloon interior. In over the wire or rapid exchange designs, a guidewire is slidably received within a guidewire lumen extending at least within a distal section of the catheter.

A lubricious coating is typically provided on the outer surface of the catheter shaft to facilitate the movement of the catheter within the patient's body lumen. Additionally, a lubricious coating may be provided on an inner surface of the shaft which defines the guidewire lumen, to facilitate the movement of a guidewire therein. The lubricious coatings generally comprise silicone, polymeric materials, or hydrophilic compounds which become lubricious after absorbing water. However, a lubricious coating with high lubricity may often have poor adhesion to the catheter shaft surface. In addition to coatings which provide lubricity, catheter shafts may be formed from a hydrophilic polymeric blend. However, one challenge has been providing high lubricity without a loss of other catheter shaft characteristics such as low profile, strength, flexibility, and case of manufacture.

Therefore, what has been needed is a balloon catheter having a lubricious shaft with improved shaft performance characteristics, which retains it's lubricity after repeated use, and which provides improved ease of manufacture. The present invention satisfies these and other needs.

SUMMARY OF THE INVENTION

The invention is directed to an intravascular catheter which has a lubricious catheter shaft formed from a polymeric blend comprising a thermoplastic polymeric component and a lubricious polymeric component. The lubricious component is immiscible in the thermoplastic component and exists as elongated fibers having a high aspect ratio. In accordance with the invention, the lubricious component exists as a separate phase of elongated fibers which provide improved lubricity to an extruded catheter shaft formed of the polymeric blend of the invention. The aspect ratio of the hydrophilic component fibers is about 10 to about 100, and preferably about 20 to about 50, and most preferably at least about 20. The high aspect ratio of the lubricious component fibers increase the surface area of the lubricious component on the surface of the catheter shall, and consequently increase the lubricity of the catheter shaft. Additionally, the lubricious component fibers are longitudinally oriented, which further enhances the effect of the lubricious component on the lubricity of the shaft.

The polymeric blend of the invention preferably comprises a minor amount of the lubricious component and a major amount of the thermoplastic component, Because the elongated fibers of the lubricious component provide improve lubricity, a minor amount of lubricious component nonetheless provides substantial lubricity to the catheter shaft formed thereby. In a presently preferred embodiment, the lubricious component comprises about 5 to about 20 percent by weight of the polymeric blend, and most preferably less than about 10 percent by weight of the blend. The weight percent of lubricious component must be sufficiently low that the immiscible lubricious component readily mixes into the matrix polymeric component.

In a presently preferred embodiment, the intravascular catheter of the invention is a balloon catheter generally comprising an elongated catheter shaft with an inflatable member on a distal portion of the chanter. The catheter shaft has an outer tubular member and an inner tubular member disposed within the outer tubular member inner lumen, with a distal extremity of tile inflatable member sealed about and secured to a distal extremity of the inner tubular member. A proximal extremity of the inflatable member is sealed about and secured to a distal extremity of the outer tubular member or the two are formed as an integral member. In a presently preferred embodiment, the lubricious catheter shaft of the invention forms the inner tubular member of a balloon catheter, so that guidewire movement therein is facilitated by the lubricity of the inner tubular member. However, the lubricious catheter shaft may form an outer member of the catheter, and thereby facilitate movement of the catheter within a body lumen of the patient.

A method of forming a lubricious catheter shaft of the invention comprises extruding the thermoplastic polymeric component and the immiscible lubricious component blend to form tubing. The tubing is stretched in a cold state (i.e. room temperature) so that the lubricious component exists as elongated fibers having a high aspect ratio, A catheter shaft formed of the polymeric blend of the invention comprising a thermoplastic polymeric component and an immiscible lubricious component has excellent lubricity. The lubricious component exists as elongated fibers having a high aspect ratio which provide improved lubricity to a catheter shaft formed therefrom. These and other advantages of the invention will become more apparent from the following detailed description of the invention and the accompanying exemplary drawings.

BRIEF DESCRIPTION OF THE DRAWINGS

FIG. 1 is an elevational view, partially in section, of a balloon catheter embodying features of the invention.

FIG. 2 is a transverse cross sectional view of the catheter shown in FIG. 1, taken along lines 2—2.

FIG. 3 is a transverse cross sectional view of the catheter shown in FIG. 1. taken along lines 3—3.

FIG. 4 is a high magnification, longitudinal cross sectional view of a section of the catheter shaft shown in FIG. 1.

FIG. 5 is a high magnification, transverse cross sectional view of the catheter shaft shown in FIG. 4, taken along lines 4—4.

DETAILED DESCRIPTION OF THE PREFERRED EMBODIMENTS

FIG. 1 illustrates an intravascular catheter 10 of the invention having a lubricious catheter shaft. The catheter generally includes an elongated catheter shaft 11 having a proximal 12 and distal 13 section, an inflatable balloon 14 on the distal section 13 of the catheter shaft 11, and an adapter 17 mounted on the proximal section 12 of shaft 11. At least a section of the catheter shaft 11 is lubricious and is formed of a polymeric blend comprising a thermoplastic polymeric component and a lubricious polymeric component. The lubricious component is immiscible in the thermoplastic component and exists as elongated fibers having a high aspect ratio.

In the embodiment illustrated in FIG. 1, the catheter shaft 11 has an outer tubular member 19 and an inner tubular member 20 disposed within the outer tubular member and defining, with the outer tubular member, inflation lumen 21. Inflation lumen 21 is in fluid communication with the interior chamber 15 of the inflatable balloon 14. The inner tubular member 20 has an inner lumen 22 extending therein which is configured to slidably receive a guidewire 23 suitable for advancement through a patient's coronary arteries. The distal extremity of the inflatable balloon 14 is sealingly secured to the distal extremity of the inner tubular member 20 and the proximal extremity of the balloon is sealingly secured to the distal extremity of the outer tubular member 19. In FIG. 1, the catheter system is illustrated within a patient's body lumen 18, with the balloon 14 in an unexpanded state. FIGS. 2 and 3 illustrate a transverse cross section of the catheter illustrated in FIG. 1 taken along lines 2—2 and 3—3, respectively.

In a presently preferred embodiment of the invention, the inner tubular member 20 is formed of the polymeric blend of the invention. The resulting lubricity of the inner tubular member 20 facilitates guidewire 23 movement within is the guidewire lumen 22 extending therein. However, other catheter sections such as a section of an outer tubular member 19 may be formed of the lubricious polymeric blend of the invention.

A variety of lubricious components may be used in the polymeric blend of the invention, including water soluble hydrophilic polymers such as polyethylene oxide, polyacrylamide, polyvinyl pyrollidone, and sulfonated polystyrene, nonhydrophilic polymers such as silicones, siloxanes and other lubricious polymers. A variety of melt processable i.e., extrudable, polymers may be used as the thermoplastic polymeric component, and in a presently preferred embodiment, the thermoplastic polymeric component is selected from the group consisting of nylon, polyethylene terephthalate, polyethylene, polypropylene, and thermoplastic elastomers. The lubricious component comprises about 5 to about 20 percent by weight of the polymeric blend, and preferably about 5 to about 10 percent by weight of the polymeric blend.

FIG. 4 illustrates a high magnification, longitudinal cross section of the lubricious inner tubular member 20 formed of the polymeric blend of the invention. FIG. 5 illustrates a transverse cross section of the inner tubular member 20 shown in FIG. 4, taken along lines 5—5. The lubricious component exists as elongated fibers 30 dispersed in the thermoplastic component 32, and having a high aspect ratio of about 10 to about 100, and preferably about 20 to about 50, and most preferably at least about 20. In the embodiment illustrated in FIG. 4, the aspect ratio of the elongated fibers 30 is about 20. In a presently preferred embodiment, the elongated fibers have a length of 1 $\mu$m to about 20 $\mu$m, and preferably about 2 $\mu$m to about 5 $\mu$m, and a diameter of about 0.1 $\mu$m to about 5 $\mu$m, and preferably about 0.2 $\mu$m to about 0.5 $\mu$m. The high aspect ratio of the elongated fibers results in improved lubricity in the lubricious catheter shaft of the invention. As illustrated in FIG. 4, the elongated fibers are longitudinally oriented following the cold stretch method of the invention. This orientation enhances the lubricity of the catheter shaft by maximizing the exposure of the lubricious polymeric component.

In the method of forming the lubricious catheter shaft of the invention, a polymeric blend comprising a thermoplastic polymeric component and an lubricious component is extruded into tubing. The lubricious component is immiscible in the thermoplastic polymeric component, and following the extrusion, the lubricious component exists as small spheres, with an aspect ratio of about 1, dispersed in the thermoplastic polymeric component. After the tubing cools to about room temperature, the tubing is elongated so that the lubricious component elongates into fibers having an aspect ratio of about 10 to about 100, and preferably about 20 to about 50, and most preferably at least about 20, to form the lubricious catheter shaft. Therefore, the tubing must be extruded with a sufficiently large wall thickness so that the tubing can be highly stretched, and thereby elongate the lubricious component. For example, tubing extruded with a wall thickness of about 0.006 to about 0.014 inch, is subsequently stretched to a final wall thickness of about 0.003 to about 0.008 inch in the cold stretch process.

The length of the dilatation catheter 10 may be about 120 to about 150 cm in length, and typically is about 135 cm in length. The outer tubular member 19 has an OD of about 0.03 to about 0.05 inch (0.76–1.27 mm) and an ID of about 0.025 to about 0.035 inch (0.635–0.899 mm). Although not shown in the drawings, the outer tubular member 19 may taper in its distal portion to a smaller OD of about 0.04 to about 0.02 inch (1.02–10.55 mm) and a smaller ID of about 0.03 to about 0.015 inch (0.762–0.381). The smaller diameter portion between the taper and the proximal extremity of the inflatable member 14 may be about 5 to about 25 cm in length.

The inner tubular member 20 has an OD ranging from about 0.018 to about 0.026 inch (0.457–0.66 mm), and the ID of the inner tubular member will usually be determined by the diameter of the guidewire 23 which is to be used with the catheter, which may range from about 0.008 to about 0.02 inch (0.203–0.51 mm). The inner diameter of the inner lumen should be about 0.002 to about 0.005 inch (0.051–0.127 mm) larger than the OD of the guidewire 23 to be 20 used. Usually there will be a family of catheters for each size of guidewire with a variety of maximum inflated inflatable member sizes, e.g., 0.5 to about 4 mm in diameter and with various working lengths ranging from about 1 to about 10 cm.

To the extent not previously described herein, the various catheter components may be formed of conventional materials. For example, a radiopaque marker on the catheter shaft may be a gold band and the adapter body may be formed of polycarbonate polymers.

EXAMPLE

Tubing having 0.025 inch inner diameter (ID) and 0.033 inch outer diameter (OD) was extruded from a polymeric blend comprising 95 weight percent nylon and 5 weight percent polyethylene oxide. The tubing was allowed to cool to room temperature (about 25° C.) and was stretched to an ID) of 0.019 inch and an OD of 0.024 inch. The aspect ratio of the polyethylene oxide fibers was about 20. The tubing thus formed showed decreased resistance to guidewire movement therein following the cold stretching as compared to tubing that was not cold stretched.

While the present invention has been described in terms of certain preferred embodiments, those skilled in the art will recognize that modifications and improvements may be made to the invention without departing from the scope thereof.

What is claimed:

1. A method of making a lubricious shaft for an intravascular catheter, comprising:
   a) providing a polymeric blend comprising a thermoplastic polymeric component and a lubricious polymeric component immiscible in the thermoplastic polymeric component;
   b) extruding the polymeric blend-to form tubing; and
   c) elongating the tubing so that the lubricious polymeric component exists as elongated fibers having an aspect ratio of about 10 to about 100, to form the lubricious catheter shaft.

2. The method of claim 1 including before step (c) the step of allowing the extruded tubing to cool to about room temperature after being extruded.

3. The method of claim 1 wherein elongating the tubing comprises cold stretching the tubing which has the lubricious polymeric component as separate spheres dispersed in the thermoplastic polymeric component.

4. The method of claim 1 wherein elongating the tubing comprises cold stretching the tubing so that the elongated tubing has the lubricious polymeric component as separate fibers dispersed in the thermoplastic polymeric component.

* * * * *